(12) United States Patent
Yuste et al.

(10) Patent No.: US 6,662,039 B2
(45) Date of Patent: *Dec. 9, 2003

(54) OPTICAL PROBING OF NEURONAL CONNECTIONS WITH FLUORESCENT INDICATORS

(75) Inventors: Rafael Yuste, New York, NY (US); Zita Peterlin, New York, NY (US)

(73) Assignee: The Trustees of Columbia University in the City of New York, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/336,026

(22) Filed: Jun. 18, 1999

(65) Prior Publication Data

US 2003/0009103 A1 Jan. 9, 2003

(51) Int. Cl.[7] .............................. A61B 6/00; G01N 33/00
(52) U.S. Cl. .................... 600/431; 250/461.2; 600/476; 800/3; 800/18; 424/9.6
(58) Field of Search .................. 600/476, 407, 600/431, 317; 250/461.2, 459.1; 436/63, 800, 805; 800/3, 18; 424/9.6

(56) References Cited

U.S. PATENT DOCUMENTS

| | | | | |
|---|---|---|---|---|
| 5,239,998 A | * | 8/1993 | Krauthamer | 600/317 |
| 5,438,989 A | * | 8/1995 | Hochman et al. | 600/426 |
| 5,756,351 A | * | 5/1998 | Isacoff et al. | 435/325 |
| 5,998,204 A | * | 12/1999 | Tsien et al. | 435/325 |
| 6,027,881 A | * | 2/2000 | Pavlakis et al. | 435/6 |
| 6,107,066 A | * | 8/2000 | Tsien et al. | 435/173.4 |

OTHER PUBLICATIONS

Smetters et al, "Detecting Action Potentials in Neoronal Populations with Calcium Imaging", Jun. 1999, Methods, vol. 18, pp. 215–221.*

Buhl E.H., Halasky K., Somogyi P. (1994). Diverse Sources of Hippocampal Unitary Inhibitory Postsynaptic Potentials and the Number of Synaptic Release Sites. *Nature* 368, 823–828. (Exhibit 1).

Katz L.C., Dalva M. (1994). Scanning Laser Photostimulation: A New Approach for Analyzing Brain Circuits. *J. Neurosci. Meth.* 54, 205–18. (Exhibit 2).

Meister M., Pine J., Baylor D.A. (1994). Multi–neuronal Signals From the Retina: Acquisition and Analysis. *J. Neurosci. Meth.* 51, 95–106. (Exhibit 3).

O'Donovan M.J., Ho S., Sholomenko G., Yee W. (1993). Real–time Imaging of Neurons Retrogradely and Anterogradely Labelled with Calcium–sensitive Dyes. *J. Neurosci. Meth.* 46 91–106. (Exhibit 4).

Schwartz T., Rabinowitz D., Unni V.K., Kumar V.S., Smetters D.K., Tsiola A., Yuste R. (1998). Networks of Coactive Neurons in Developing Layer I. *Neuron* 20, 541–552. (Exhibit 5).

(List continued on next page.)

*Primary Examiner*—Ruth S. Smith
(74) *Attorney, Agent, or Firm*—John P. White; Cooper & Dunham LLP (57) ABSTRACT

This invention provides methods of identifying a connection between a first neuron and a second neuron or plurality of neurons in a neural tissue slice with a fluorescent indicator. This invention also provides a method of detecting the effect of a neuromodulator on a connection between a first neuron and a second neuron or a plurality of neurons forming a circuit; methods of identifying an inhibitory connection between a first neuron and a second neuron or plurality of neurons; and a method of identifying a connection between a first neuron and a second neuron or plurality of neurons in vivo or in vitro.

22 Claims, 7 Drawing Sheets

OTHER PUBLICATIONS

Siegel M.S., Isacoff E.Y. (1997). A Genetically Encoded Optical Probe of Membrane Voltage. *Neuron* 19, 735–41. (Exhibit 6).

Tsien R.Y. (1981). A non–disruptive Technique for Loading Calcium Buffers and Indicators into Cells. *Nature.* 290, 527–528. (Exhibit 7).

Yuste R., Katz L.C. (1991). Control of Postsynaptic $Ca^{2+}$ Influx In Developing Neocortex by Excitatory and Inhibitory Neurotransmitters. *Neuron* 6, 333–344. (Exhibit 8).

* cited by examiner

OPTICAL PROBING OF NEURONAL CONNECTIONS WITH FLUORESCENT INDICATORS

This invention was made with support under Grant No. EY 111787 from the NIH National Eye Institute. Accordingly, the United States Government has certain rights in the invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

A major experimental difficulty in unraveling neuronal circuits is the identification of the postsynaptic targets of a given neuron. While ultrastructural reconstructions of target cells are labor intensive, simultaneous recordings from pairs of randomly chosen cells have been recently used to identify connected pairs of neurons. The present study describes a novel approach using fluorescent (e.g. calcium) imaging of populations of neurons that allows us to rapidly identify many postsynaptic targets of any given neuron in a brain slice. Combining bulk-loading of fluorescent (e.g. calcium) indicators with optimal imaging and analysis protocols, the present study demonstrates that neurons that have somatic calcium transients time-locked to the spikes of a stimulated neuron are monosynaptically connected to it. This method can be supplemented with recordings from identified postsynaptic neurons and can be applied systematically to quickly reconstruct circuits from many regions of the CNS.

One of the most neglected aspects of systems neurobiology is the reconstruction of specific circuit diagrams involved in the particular function studied. It is evident that the knowledge of the detailed circuit diagram is necessary to fully understand the computations carried out by any nervous system. Yet, even in cases where the nature of the computation is clear, the detailed implementation of the computational algorithms by circuits of neurons remains mysterious (Heiligenberg, 1991). A direct approach to decipher a particular circuit is its reconstruction with electron microscopy. Such a program has only been successfully achieved in the nervous system of C. elegans, which has only 302 neurons and with a stereotyped connectivity from animal to animal (White et al., 1986). Until the advent of automatic electron microscopy reconstructions (Macagno et al., 1979; White et al., 1993), these efforts were impractical in most nervous systems due to the number of neurons and the laboriousness of the task. More specifically, one of the major practical problems facing the electron microscopists is identifying the neurons targeted by a particular axon from an identified neuron. Only detailed serial thin-section reconstructions of the dendritic tree of the target neuron can reveal, in most instances, its identity (McGuire et al., 1991; Czeiger and White, 1993).

In recent decades, the use of multielectrode electrical recordings has provided an alternative strategy to characterizing circuit connectivity. Extracellular recordings using microelectrode arrays permit the simultaneous recordings of dozen or hundreds of neurons (Meister et al., 1994). While extremely valuable for reconstructing the spatio-temporal dynamics of a neuronal population (Meister et al., 1991), this approach, however, suffers the disadvantage of sampling only a small proportion of the neurons in a given area and also of lacking anatomical information about the particular cells responsible for the spikes. Another approach to the functional circuitry is to perform dual intracellular recordings from pairs of connected neurons. This has been achieved in brain slices by combining intracellular recording and staining with electron microscopy reconstructions and confirmation of the contact (Gulyas et al., 1993; Buhl et al., 1994; Deuchards et al., 1994). In principle, this approach could accurately characterize the functional connectivity between pairs of cortical neurons. Nevertheless, given the difficulty of obtaining recordings of pairs of connected neurons, the many different types of neurons, and the low probability that any given pair—chosen at random—is actually connected, would make only a labor-intensive effort with semi-automated experimental procedures successful.

The studies herein describe a novel method to identify postsynaptic targets from a given neuron in brain slices stained with fluorescent (e.g. calcium) indicators. This technique builds on previous work that showed that optical monitoring of the activity of a neuronal population is feasible with calcium indicators (Yuste and Katz, 1991; O'Donovan et al., 1993). Improvements in bulk loading methods for calcium indicators (Tsien, 1981; Schwartz et al., 1998; Yuste, 1999) and the ubiquitous presence of calcium channels and their activation by action potentials (Yuste and Denk, 1995; Helmchen et al., 1996) makes possible the optical detection of action potentials in populations of neurons (Smetters et al., 1999) and consequently enables the detection of which neurons produce an action potential in response to stimulation of another neuron.

SUMMARY OF THE INVENTION

This invention provides a method of identifying a connection between a first neuron and a second neuron or plurality of neurons comprising of: a) loading neurons in a neural tissue slice with a fluorescent indicator; b) optically detecting an image of the fluorescent indicator-loaded neurons; c) stimulating a first neuron in the neural tissue slice to elicit one action potential or many (multiple) action potentials from said neuron; and d) optically detecting a change in intensity of the fluorescent indicator in the image at a second neuron or plurality of neurons of the neural tissue slice in response to the action potential(s) elicited from the first neuron in step (c), wherein detection of a transient decrease in the intensity of the fluorescent indicator in the image at the second neuron or plurality of neurons indicates the activation in the second neuron or plurality of neurons, thereby identifying the connection between the second neuron or plurality of neurons and the first neuron.

This invention provides a method of detecting the effect of a neuromodulator on a connection between a first neuron and a second neuron or a plurality of neurons forming a circuit which comprises: a) loading neurons in a neural tissue slice with a fluorescent indicator; b) optically detecting an image of the fluorescent indicator-loaded neurons; c) administering a neuromodulator to the neural tissue slice to modulate the eliciting of one action potential or many (multiple) action potentials from the neurons or the plurality of neurons forming the circuit and to modulate the activity of a synaptic connection or plurality of connections between the neurons; and d) optically detecting a change in intensity of the fluorescent indicator in the image at the second neuron or in the plurality of neurons of the neural tissue slice in response to the action potential(s) elicited from the first neuron in step (c), wherein detection of a transient decrease or increase in the intensity of the fluorescent indicator in the image at the second neuron or the plurality of neurons indicates an increase or decrease, respectively, in the acivation of the second neuron or plurality of neurons, thereby identifying the effect of the neuromodulator on the connection between the first neuron and the second neuron or between the plurality of neurons forming the circuit.

This invention provides a method of identifying an inhibitory connection between a first neuron and a second neuron or plurality of neurons comprising of: a) loading neurons in a neural tissue slice with a fluorescent indicator; b) optically detecting an image of the fluorescent indicator-loaded neurons under a high background of spontaneous activity; c) stimulating a first inhibitory neuron in the neural tissue slice to elicit one action potential or many (multiple) action potentials from said neuron; and d) optically detecting a change in intensity or lack thereof (no intensity) of the fluorescent indicator in the image at a second neuron or plurality of neurons of the neural tissue slice in response to the action potential(s) elicited from the first inhibitory neuron in step (c), wherein detection of a transient decrease in the intensity of the fluorescent indicator in the image at the second neuron or plurality of neurons indicates an inactivation of the second neuron or plurality of neurons, thereby identifying the inhibitory connection between the first inhibitory neuron and the second neuron or plurality of neurons.

This invention provides a method of detecting the effect of a neuromodulator on an inhibitory connection between a first neuron and a second neuron or a plurality of neurons forming a circuit which comprises: a) loading neurons in a neural tissue slice with a fluorescent indicator; b) optically detecting an image of the fluorescent indicator-loaded neurons; c) administering a neuromodulator to the neural tissue slice to modulate the eliciting of one action potential or many (multiple) action potentials from the neurons or the plurality of neurons forming the circuit and to modulate the activity of a synaptic connection or plurality of connections between the neurons; and d) optically detecting a change in intensity of the fluorescent indicator in the image at the second neuron or in the plurality of neurons of the neural tissue slice in response to the action potential(s) elicited from the first neuron in step (c), wherein detection of a transient decrease or increase in the intensity of the fluorescent indicator in the image at the second neuron or the plurality of neurons indicates, indicates an activation or inactivation, respectively, of the second neuron or plurality of neurons, thereby identifying the effect of the neuromodulator on the inhibitory connection between the first neuron and the second neuron or between the plurality of neurons forming the circuit.

This invention provides a method of identifying an inhibitory connection between a first neuron and a second neuron or plurality of neurons comprising of: a) loading neurons in a neural tissue slice with a chloride indicator; b) optically detecting an image of the chloride indicator-loaded neurons; c) stimulating a first inhibitory neuron in the neural tissue slice to elicit one action potential or many action potentials from said neuron; and d) optically detecting a change in intensity of the chloride indicator in the image at a second neuron or plurality of neurons of the neural tissue slice in response to the action potential(s) elicited from the first inhibitory neuron in step (c), wherein detection of a transient change in the intensity of the chloride indicator in the image at the second neuron or plurality of neurons indicates an inhibitory effect in the second neuron or plurality of neurons, thereby identifying the inhibitory connection between the first inhibitory neuron and the second neuron or plurality of neurons.

This invention provides a method of detecting the effect of a neuromodulator on an inhibitory connection between a first neuron and a second neuron or a plurality of neurons forming a circuit which comprises: a) loading neurons in a neural tissue slice with a chloride indicator; b) optically detecting an image of the chloride indicator-loaded neurons; c) administering a neuromodulator to the neural tissue slice to modulate the eliciting of one action potential or many (multiple) action potentials from the neurons or the plurality of neurons forming the circuit and to modulate the activity of a synaptic connection or plurality of connections between the neurons; and d) optically detecting a change in intensity of the chloride indicator in the image at the second neuron or in the plurality of neurons of the neural tissue slice in response to the action potential(s) elicited from the first neuron in step (c), wherein detection of a transient change in the intensity of the chloride indicator in the image at the second neuron or the plurality of neurons indicates, indicates an inhibitory effect on the second neuron or plurality of neurons, thereby identifying the effect of the neuromodulator on the inhibitory connection between the first neuron and the second neuron or between the plurality of neurons forming the circuit.

This invention provides a method of identifying a connection between a first neuron and a second neuron or plurality of neurons in vivo comprising of: a) genetically encoding a transgenic animal to express GFP based-indicators in neural tissue; b) optically detecting an image of the GFP-based indicator in neurons of a neural tissue of the transgenic mouse using two-proton microscopes; c) stimulating a first neuron or a neural circuit in the neural tissue to elicit multiple action potentials from said neuron or said neural circuit; and d) optically detecting a change in intensity of the GFP-based indicator in the image at a second neuron or plurality of neurons of the neural tissue in response to the multiple action potentials elicited from the first neuron in step (c), wherein detection of a transient change in the intensity of the GFP-based indicator in the image at the second neuron or plurality of neurons indicates activation or inactivation of the second neuron or plurality of neurons, thereby identifying the connection between the second neuron or plurality of neurons and the first neuron.

This invention provides a method of detecting the effect of a neuromodulator on a connection between a first neuron and a second neuron or plurality of neurons in vivo which comprises: a) genetically encoding a transgenic animal to express GFP based-indicators in neural tissue; b) optically detecting an image of the GFP based indicator in neurons of a neural tissue in the transgenic mouse using a conventional microscope or a two-proton microscope; c) administering a neuromodulator to the neural tissue of the transgenic animal to modulate the eliciting of one action potential or many (multiple) action potentials from the neurons or the plurality of neurons forming the circuit and to modulate the activity of a synaptic connection or plurality of connections between the neurons; and d) optically detecting a change in intensity of the GFP-based indicator in the image at a second neuron or plurality of neurons of the neural tissue in response to the action potential(s) elicited from the first neuron in step (c), wherein detection of a transient change in the intensity of the GFP-based indicator in the image at the second neuron or plurality of neurons indicates activation or inactivation (inhibition) of the second neuron or plurality of neurons, thereby identifying the effect of the neuromodulator on the connection between the first neuron and the second neuron or plurality of neurons in vivo.

This invention provides a method of identifying a connection between a first neuron and a second neuron or plurality of neurons in vitro comprising of: a) optically detecting an image of the GFP-based indicator in neurons of a neural tissue slice from a transgenic animal whose neural tissue expresses GFP-based indicators using a conventional microscope or a two-proton microscope; b) stimulating a first neuron or a neural circuit in the neural tissue slice to elicit multiple action potentials from said neuron or said neural circuit; and c) optically detecting a change in intensity of the GFP-based indicator in the image at a second neuron or plurality of neurons of the neural tissue in response to the multiple action potentials elicited from the first neuron in step (b), wherein detection of a transient change in the intensity of the GFP-based indicator in the image at the second neuron or plurality of neurons indicates activation or inactivation (inhibition) of the second neuron or plurality of neurons, thereby identifying the connection between the second neuron or plurality of neurons and the first neuron.

This invention provides a method of detecting the effect of a neuromodulator on a connection between a first neuron and a second neuron or plurality of neurons in vitro which comprises: a) optically detecting an image of the GFP-based indicator in neurons of a neural tissue slice from a transgenic animal whose neural tissue expresses GFP-based indicators using a conventional microscope or a two-proton microscope; b) administering a neuromodulator to the neural tissue of the transgenic animal to modulate the eliciting of one action potential or many (multiple) action potentials from the neurons or the plurality of neurons forming the circuit and to modulate the activity of a synaptic connection or plurality of connections between the neurons; and c) optically detecting a change in intensity of the GFP-based indicator in the image at a second neuron or plurality of neurons of the neural tissue in response to the action potential(s) elicited from the first neuron in step (b), wherein detection of a transient change in the intensity of the GFP-based indicator in the image at the second neuron or plurality of neurons indicates activation or inhibition of the second neuron or plurality of neurons, thereby identifying the the effect of the neuromodulator on the connection between the first neuron and the second neuron or plurality of neurons in vitro.

BRIEF DESCRIPTION OF THE FIGURES

FIGS. 1A–C. Loading mature cortical slices with fura-2 AM.

FIGS. 2A–2D Response of a "follower" neuron are time-locked to the stimulation of a "trigger" cell. FIG. 2D: Image of the fluorescence measurements from the entire photodiode array. The positions of cell 1 and 2 are marked by numbers. Note how two other regions of the slice also show fluorescence decreases triggered by the stimulation of neurons 1. The membrane voltage of neuron 1, marked as V, was recorded on one of the 8 non-optical input channels. The area imaged was a region of layer ⅔ approximately 250×250 $\mu$m with the pial surface to the left. The distance between the somata of the pair of putatively connected neurons is ca. 90 $\mu$m. The experiment was carried out in a P18 mouse coronal cortical slice under standard ACSF (2 mM $Ca^{2+}$ and 1 mM Mg2+). The slice was stained with fura-2 AM as described above.

FIGS. 3A–3C. Recording of a "trigger" and "follower" neuron. FIG. 3B: Localization of putatively connected cells using the processed fluorescent movie. The trigger cell was filled with 50 $\mu$M fura-K and the slice maintained in magnesium-free ACSF (2 mM $Ca^{2+}$, 0 mM $Mg^{2+}$). 500 ms into the imaging, 10 depolarizing current steps (0.80 nA, 5 ms) were used to elicit a train of 10 action potentials at 40 Hz from the trigger cell. In this frame of the processed movie, corresponding to the onset of the train, two darker regions of decreasing fluorescence can be noted at the somas of the trigger and follower cells. These regions are even more salient when the time-locked nature of the transient, localized darkenings can be appreciated in the animated movie.

FIGS. 4A–4C Anatomical confirmation of monosynaptic connection between the "trigger" and "follower". FIGS. 4B, C. Higher magnification of marked regions in FIG. 4A. Physical contacts between the axon of the "trigger" cell (white arrow) and two dendrites of the "follower" (black arrows) are observed. Scale bar=10 $\mu$m.

DETAILED DESCRIPTION OF THE INVENTION

This invention provides a method of identifying a connection between a first neuron and a second neuron or plurality of neurons comprising of: a) loading neurons in a neural tissue slice with a fluorescent indicator; b) optically detecting an image of the fluorescent indicator-loaded neurons; c) stimulating a first neuron in the neural tissue slice to elicit one action potential or many (multiple) action potentials from said neuron; and d) optically detecting a change in intensity of the fluorescent indicator in the image at a second neuron or plurality of neurons of the neural tissue slice in response to the action potential(s) elicited from the first neuron in step (c), wherein detection of a transient decrease in the intensity of the fluorescent indicator in the image at the second neuron or plurality of neurons indicates the activation in the second neuron or plurality of neurons, thereby identifying the connection between the second neuron or plurality of neurons and the first neuron.

As used herein "activation" is the depolarization produced in the second neuron(s).

In an embodiment of the above-described method identifying a connection between a first neuron and a second neuron or plurality of neurons the fluorescent indicator is a fluorescent dye. In another embodiment of the method the fluorescent indicator is selected from the group consisting of fura-2 AM, calcium green AM, Oregon BAPTA Green AM and indo-2 AM. In a further embodiment of the method the neural tissue is stimulated in step (b) with repeated pulses of depolarizing current at 10–100 Hz. In another embodiment of the method the neural tissue is selected from the group consisting of mammalian central nrevous system and peripheral neurons.

In an embodiment of the method the image in step (a) is obtained with any camera. In an embodiment the camera may be a cool charge-coupled device (CCD) camera.

In another embodiment of the above-described the optical detection of step (d) is determined by a measuring a percent change over time in the calcium indicator, said percent change calculated as $\Delta F/F = ((F_0 - B_0) - (F_1 - B_1))/F_0 - B_0$, wherein $F_0$ is the fluorescence signal of the fluorescent indicator after loading and $B_0$ is the background fluorescence after loading, $F_1$ is the fluorescence signal of the fluorescent indicator at one time point after stimulation, and $B_1$ is the background fluorescence at said time point after stimulation.

The above-described method of identifying a connection between a first neuron and a second neuron or plurality of neurons, wherein the optical detection of step (d) is determined by a measuring a percent change over time in the calcium indicator, said percent change calculated as $\Delta F/F = ((F_0 - B_0) - (F_1 - B_1))/F_0 - B_0$, wherein $_0F$ is the fluorescence signal of the fluorescent indicator after loading and $B_0$ is the background fluorescence after loading, $F_1$ is the fluorescence signal of the fluorescent indicator at one time point after stimulation, and $B_1$ is the background fluorescence at said time point after stimulation, wherein the percent change is calculated by a computer-assisted method. The computer assisted method, designated "Zap-summed/avg movie", comprises the following steps:

```
Show Image
Select All
Query
If
Set Variable            var 2 = nframes to sum
Extract Image Sizes     get nframes
Set Variable            var 7 = nframes
Dispose Window
Set Variable            var 1 = var2 − #1
Set Variable            var 3 = nframes/framesum
Sequence to Frames
Dispose Window
frame addn loop         loop over frames
Rename Window
Change Window
Image Arithmetic
Dispose Window
Loop
Rename Window
Change Window
Loop
Frames to Sequence
Show Image
Set Variable
Extract Image Sizes     get nframes
Set Variable
Dispose Window
Sequence to Frames
Change Window
Duplicate Window
Change Window
top.fura
Image Arithmetic        (fr2 − fr1)
Image Arithmetic        / (variable * fr1)
Change Window
Loop
Change Window
Dispose Window
Dispose Window
Frames to Sequence
Change Window
Show Image
Move Window
Dispose Window
Alert
Animate
shunt to end
END
```

The above-described computer assisted method may be a computer program written in IPLab or NIH Image. One of skill in the art will readily be able to use imaging software other than the program described herein and also write programs other than the program set for the herein for this calculation.

This invention provides a method of detecting the effect of a neuromodulator on a connection between a first neuron and a second neuron or a plurality of neurons forming a circuit which comprises: a) loading neurons in a neural tissue slice with a fluorescent indicator; b) optically detecting an image of the fluorescent indicator-loaded neurons; c) administering a neuromodulator to the neural tissue slice to modulate the eliciting of one action potential or many (multiple) action potentials from the neurons or the plurality of neurons forming the circuit and to modulate the activity of a synaptic connection or plurality of connections between the neurons; and d) optically detecting a change in intensity of the fluorescent indicator in the image at the second neuron or in the plurality of neurons of the neural tissue slice in response to the action potential(s) elicited from the first neuron in step (c), wherein detection of a transient decrease or increase in the intensity of the fluorescent indicator in the image at the second neuron or the plurality of neurons indicates an increase or decrease in the acivation of the second neuron or plurality of neurons, thereby identifying the effect of the neuromodulator on the connection between the first neuron and the second neuron or between the plurality of neurons forming the circuit.

In an embodiment of the above-described method of detecting the effect of a neuromodulator on a connection between a first neuron and a second neuron or a plurality of neurons forming a circuit the neuromodulator is a neurochemical agent. The neurochemical agents may be selected from drugs which are candidates for therapeutic intervention. As used herein a "neuromodulator" is defined as an agonist or an antagonist of receptors present in neurons. Neuromodulators may be pharmaceutical agents which may be used to treat neurological diseases or psychiatric disorders, including but not limited to diseases and disorders such as epilepsy or schizophrenia.

This invention provides a method of identifying an inhibitory connection between a first neuron and a second neuron or plurality of neurons comprising of: a) loading neurons in a neural tissue slice with a fluorescent indicator; b) optically detecting an image of the fluorescent indicator-loaded neurons under a high background of spontaneous activity; c) stimulating a first inhibitory neuron in the neural tissue slice to elicit one action potential or many (multiple) action potentials from said neuron; and d) optically detecting a change in intensity of the fluorescent indicator in the image at a second neuron or plurality of neurons of the neural tissue slice in response to the action potential(s) elicited from the first inhibitory neuron in step (c), wherein detection of a transient decrease in the intensity of the fluorescent indicator in the image at the second neuron or plurality of neurons indicates an inactivation of the second neuron or plurality of neurons, thereby identifying the inhibitory connection between the first inhibitory neuron and the second neuron or plurality of neurons.

The high background spontaneous activity may be elicited by both bath application of exitatory agents or by disinhibition of the brain slice.

This invention provides a method of detecting the effect of a neuromodulator on an inhibitory connection between a first neuron and a second neuron or a plurality of neurons forming a circuit which comprises: a) loading neurons in a neural tissue slice with a fluorescent indicator; b) optically detecting an image of the fluorescent indicator-loaded neurons; c) administering a neuromodulator to the neural tissue slice to modulate the eliciting of one action potential or many (multiple) action potential(s) from the neurons or the plurality of neurons forming the circuit and to modulate the activity of a synaptic connection or plurality of connections between the neurons; and d) optically detecting a change in intensity of the fluorescent indicator in the image at the second neuron or in the plurality of neurons of the neural tissue slice in response to the action potential(s) elicited from the first neuron in step (c), wherein detection of a transient change (either a decrease or an increase) in the intensity of the fluorescent indicator in the image at the second neuron or the plurality of neurons, indicates an activation or inactivation, respectively, of the second neuron or plurality of neurons, thereby identifying the effect of the neuromodulator on the inhibitory connection between the first neuron and the second neuron or between the plurality of neurons forming the circuit.

This invention provides a method of identifying an inhibitory connection between a first neuron and a second neuron or plurality of neurons comprising of: a) loading neurons in a neural tissue slice with a chloride indicator; b) optically detecting an image of the chloride indicator-loaded neurons; c) stimulating a first inhibitory neuron in the neural tissue slice to elicit one action potential or many (multiple) action potentials from said neuron; and d) optically detecting a change in intensity of the chloride indicator in the image at a second neuron or plurality of neurons of the neural tissue slice in response to the action potential(s) elicited from the first inhibitory neuron in step (c), wherein detection of a transient change in the intensity of the chloride indicator in the image at the second neuron or plurality of neurons indicates an inhibitory effect in the second neuron or plurality of neurons, thereby identifying the inhibitory connection between the first inhibitory neuron and the second neuron or plurality of neurons. The transient change in the intensity of the chloride indicator in the image at the second neuron or plurality of neurons may be either an increase or a decrease in the intensity of the chloride indicator. A change in the chloride concentration, i.e. either an increase or decrease will indicate the inhibitory effect.

In an embodiment of the above-desctribed method of identifying an inhibitory connection between a first neuron and a second neuron or plurality of neurons the chorine indicator is selected from the group consisting of molecular probes such as MEQ.

This invention provides a method of detecting the effect of a neuromodulator on an inhibitory connection between a first neuron and a second neuron or a plurality of neurons forming a circuit which comprises: a) loading neurons in a neural tissue slice with a chloride indicator; b) optically detecting an image of the chloride indicator-loaded neurons; c) administering a neuromodulator to the neural tissue slice to modulate the eliciting of one action potential or many (multiple) action potentials from the neurons or the plurality of neurons forming the circuit and to modulate the activity of a synaptic connection or plurality of connections between the neurons; and d) optically detecting a change in intensity of the chloride indicator in the image at the second neuron or in the plurality of neurons of the neural tissue slice in response to the action potential(s) elicited from the first neuron in step (c), wherein detection of a transient change in the intensity of the chloride indicator in the image at the second neuron or the plurality of neurons indicates, indicates an inhibitory effect on the second neuron or plurality of neurons, thereby identifying the effect of the neuromodulator on the inhibitory connection between the first neuron and the second neuron or between the plurality of neurons forming the circuit. The transient change in the intensity of the chloride indicator in the image at the second neuron or the plurality of neurons may be a decrease or an increase in the intensity of the chloride indicator. The change in the chloride concentration, i.e. either an increase or decrease, will indicate the inhibitory effect.

This inventiion provides a method of identifying a connection between a first neuron and a second neuron or plurality of neurons in vivo comprising of: a) genetically encoding a transgenic mouse to express GFP based-indicators in neural tissue; b) optically detecting an image of the GFP-based indicator in neurons of a neural tissue in the transgenic mouse using a conventional microscope or a two-proton microscope; c) stimulating a first neuron or a neural circuit in the neural tissue to elicit one action potential or many (multiple) action potentials from said neuron or said neural circuit; and d) optically detecting a change in intensity of the GFP-based indicator in the image at a second neuron or plurality of neurons of the neural tissue in response to the action potential(s) elicited from the first neuron in step (c), wherein detection of a transient change in the intensity of the GFP-based indicator in the image at the second neuron or plurality of neurons indicates activation of the second neuron or plurality of neurons, thereby identifying the connection between the second neuron or plurality of neurons and the first neuron.

GPF-based indicators are transfected into the tissue using biolistics, e.g. pressure assisted transfection of neurons or with transgenic technology with which one of skill in the art will be familiar. In an embodimet of the above-described method of identifying a connection between a first neuron and a second neuron or plurality of neurons in vivo the GFP-based indicator is selected from cameleons, calcium indicators based on GFP calmodulin, or FLASH, voltage indicators based on membrane channels.

This invention provides a method of detecting the effect of a neuromodulator on a connection between a first neuron and a second neuron or plurality of neurons in vivo which comprises: a) genetically encoding a transgenic animal to express GFP based-indicators in neural tissue; b) optically detecting an image of the GFP based indicator in neurons of a neural tissue in the transgenic mouse using a conventional microscope or a two-proton microscope; c) administering a neuromodulator to the neural tissue of the transgenic animal to modulate the eliciting of one action potential or many (multiple) action potentials from the neurons or the plurality of neurons forming the circuit and to modulate the activity of a synaptic connection or plurality of connections between the neurons; and d) optically detecting a change in intensity of the GFP-based indicator in the image at a second neuron or plurality of neurons of the neural tissue in response to the action potential(s) elicited from the first neuron in step (c), wherein detection of a transient change in the intensity of the GFP-based indicator in the image at the second neuron or plurality of neurons indicates activation or inhibition of the second neuron or plurality of neurons, thereby identifying the effect of the neuromodulator on the connection between the first neuron and the second neuron or plurality of neurons in vivo. The transient change in the intensity of the GFP-based indicator in the image at the second neuron or the plurality of neurons may be a decrease or an increase in the intensity of the GFP-based indicator. The transient change will indicate activation or inactivation of the second neuron or plurality of neurons.

This invention provides a method of identifying a connection between a first neuron and a second neuron or plurality of neurons in vitro comprising of: a) optically detecting an image of the GFP-based indicator in neurons of a neural tissue slice from a transgenic animal whose neural tissue expresses GFP-based indicators using a conventional microscope or a two-proton microscope; b) stimulating a first neuron or a neural circuit in the neural tissue slice to elicit multiple action potentials from said neuron or said neural circuit; and c) optically detecting a change in intensity of the GFP based indicator in the image at a second neuron or plurality of neurons of the neural tissue in response to the multiple action potentials elicited from the first neuron in step (b), wherein detection of a transient change in the intensity of the GFP based indicator in the image at the second neuron or plurality of neurons indicates activation of the second neuron or plurality of neurons, thereby identifying the connection between the second neuron or plurality of neurons and the first neuron.

Either a conventional microscope or a two-proton microscope may be used for the optical detection of transient changes in any of the above-described methods, i.e. increase or decrease in the indicators used in said methods.

This invention provides a method of detecting the effect of a neuromodulator on a connection between a first neuron and a second neuron or plurality of neurons in vitro which comprises: a) optically detecting an image of the GFP-based indicator in neurons of a neural tissue slice from a transgenic animal whose neural tissue expresses GFP-based indicators using a conventional microscope or a two-proton microscope; b) administering a neuromodulator to the neural tissue of the transgenic animal to modulate the eliciting of one action potential or many (multiple) action potentials from the neurons or the plurality of neurons forming the circuit and to modulate the activity of a synaptic connection or plurality of connections between the neurons; and c) optically detecting a change in intensity of the GFP-based indicator in the image at a second neuron or plurality of neurons of the neural tissue in response to the action potential(s) elicited from the first neuron in step (b), wherein detection of a transient change in the intensity of the GFP-based indicator in the image at the second neuron or plurality of neurons indicates activation or inhibition of the second neuron or plurality of neurons, thereby identifying the the effect of the neuromodulator on the connection between the first neuron and the second neuron or plurality of neurons in vitro. The transient change in the intensity of the GFP-based indicator in the image at the second neuron or the plurality of neurons may be a decrease or an increase in the intensity of the GFP-based indicator which indicates activation or inactivation of the second neuron or the plurality of neurons.

This invention will be better understood from the Experimental Details which follow. However, one skilled in the art will readily appreciate that the specific methods and results discussed are merely illustrative of the invention as described more fully in the claims which follow thereafter.

Methods and Results

This method consist of (i) loading (staining) populations of neurons in brain slices with fluorescent indicators such as fura-2 AM and (ii) imaging dozens of loaded cells during whole-cell stimulation of a particular neuron (the "trigger" cell). On-line analysis is used to determine if any other neurons (the "follower" cells) show a calcium transient time-locked to the firing of the "trigger" cell. After detection, a chosen "follower" cell is patched and a similar experiment is repeated. Histological processing is carried out on the fixed specimens. A detailed explanation of the experiment and some representative results follows.

Loading neurons in mature cortical slices with fura 2-AM.

Brain slices are made from the primary visual cortex of postnatal day (PND) 12–23 C57BL6 mice. Mice are anesthetized with Ketamine/Xylazine (120 mg/kg, 10 mg/kg respectively). Animals are decapitated and the brain is quickly removed and placed into cold ACSF (126 mM NaCl, 3 mM KCl, 26 mM NaHCO$_3$, 1 mM NaH$_2$PO$_4$, 2 mM CaCl$_2$, 2 mM MgSO$_4$, 10 mM Dextrose, bubbled with 95% O$_2$/5% CO$_2$). Coronal slices, 300–400 μm thick, are cut using a vibratome (TPI) and are incubated at 35° C. for 30 minutes in a submerged slice chamber. Slices are then incubated at room temperature (~25° C.) for up to 12 hours.

Figure 1A:
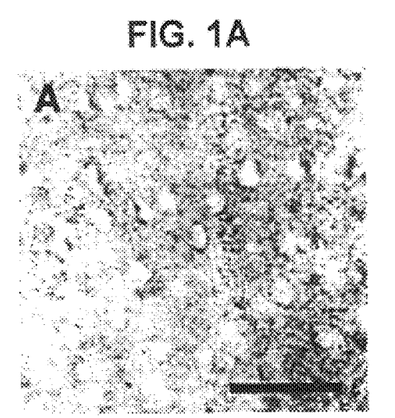
FIGS. 1A–B. DIC (left) and fluorescence (right) images of the upper layers of a coronal slice taken from the visual cortex of a P16 mouse. Pial surface to the top left. The slice was loaded with fura-2 AM using a concentrated incubation protocol (see infra). Note how the somata and even some primary dendrites from most neurons in the plain of focus are labeled. Scale bar=50 $\mu$m.
Figure 1B:
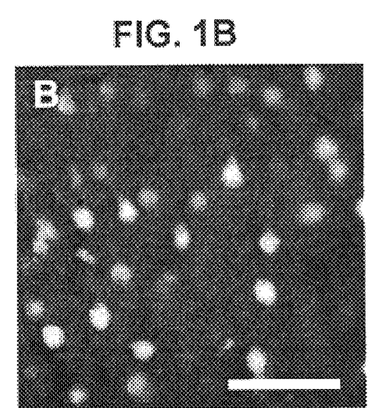
Figure 1C:
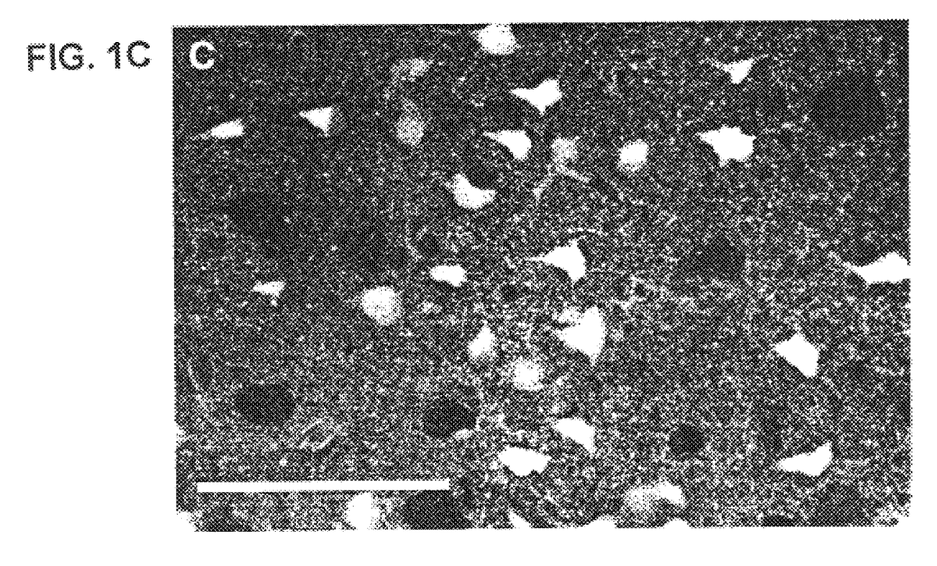
FIG. 1C. Similar fluorescence image of the upper layers of a coronal slice taken from the visual cortex of a P23 mouse loaded with the dual incubation method. Action-potential induced calcium transients were succesfully recorded from these neurons. Scale bar=50 $\mu$m.

For staining, slices are transferred to a staining chamber, which consists of a small vial with a carbogen line, where they are incubated with the acetoxymethyl (AM) ester form of fura-2 (Molecular Probes). Previous work described that diluted solutions of AM-esters load (stain) populations of cells in developing cortex (<P7 rats or mice), but the labeling becomes scarce with increasing age of the animal (Yuste and Katz, 1991). After years of experimenting with different loading protocols, it was found that concentrated DMSO solutions of the AM indicators help in loading slices from more mature animals (Schwartz et al., 1998; Smetters et al., 1999; Yuste, 1999). The current protocol is a double incubation: (i) an initial incubation with 2 μl of a 1 mM fura-2 AM (in 100% DMSO) solution for 2 minutes and then (ii) a second incubation in 3 ml of oxygenated 10 μM fura-2 AM in ACSF for 60 min. Both incubations are done in the dark. This protocol reliably loads population of neurons in cortical slices from mice as old as P23 with concentrations of fura-2 of approximately 50 μM (see below). As far as it can be assessed, the loading is not specific for any particular type of neuron (Schwartz et al., 1998; Smetters et al., 1999). Here identified are both pyramidal and non-pyramidal neurons equally loaded and comparisons with DIC images of the same fields shows the homogeneity of loading (FIG. 1).

One of skill will be familiar with various techniques for loading of fluorescent indicators. Accordingly, loading protocols are not limited to the above-described protocol, which is but one example of loading methods.

Imaging of Loaded Neurons and Intracellular Stimulation of "Trigger" Cell.

After loading, slices are placed in a submerged recording chamber mounted on the stage of an upright microscope (BX50WI, Olympus). All experiments are done at room temperature. Fluorescent images of fura-2 loaded neurons are taken with a cCCD camera (Micromax, Princeton Instruments) equipped with a frame transfer chip (EEV 512, Kodak) or an hexagonal photodiode array with 464 pixels (PDA, Universal Imaging). To maximize the number of imaged neurons a 20×/0.5 NA water immersion objective (Olympus) is used. Image acquisition is typically 25 msec/frame and each pixel is digitized at 12 bits. Camera images are acquired, stored and analyzed using a Macintosh 7100 (Apple Computers, Cupertino, Calif.) computer and IPLab software (Signal Analytics). Signals from the photodiodes are amplified, sampled at 1.6 KHz and analyzed using Neuroplex (Universal Imaging). For imaging of the calcium transients a 380 nm excitation, a 395 nm dichroic and a 510 emission filter (Chroma) are used. Also imaged is each neuron at the isosbestic excitation of 365 nm during every experiment to assess the approximate $[Ca^{2+}]_i$ and therefore monitor the health of the cells. The 365 nm images are used to estimate the intracellular concentration of fura-2, using the fluorescence of the patched cell (which has a known concentration of fura-2) as a calibration. For most neurons, after correcting for background fluorescence and focus, an intracellular concentration of indicator of approximately 40–50 $\mu$M was estimated. These values, obtained from experiments with good loading at PND 12–23, obviously depend crucially on many factors that affect loading, such as age, incubation time and health of the slices. Changes in fluorescence in multiple cells were analyzed with a program written in IPLab. The fluorescence change over time is defined as $\Delta F/F=(F_0-F_1)/(F_0)$ and, for the analysis of the AM loaded cells fluorescence change was defined as $\Delta F/F=((F_0-B_0)-(F_1-B_1))/(F_0-B_0)$, expressed in %, where $F_1$ and B are fluorescence in the somata and background fluorescence, respectively, at any given timepoint, and $F_0$ and $B_0$ are fluorescence and background at the beginning of the experiment.

For stimulation, pyramidal neurons are identified by differential interference contrast (DIC). Whole-cell patch clamp recordings [whole-cell pipettes to stimulate and record the activity of a neuron] are performed using 3–7 MOhm pipettes, filled with intracellular solution containing (mM): 110–150 K-gluconate, 0–20 KCl, 4–10 NaCl, 10 HEPES, 0–50 MgATP and 0.05 fura-2 potassium salt. A gigaohm seal is formed in voltage-clamp by pressing the pipette gently against the soma of a neuron and providing light suction. Whole-cell recordings developed within 1–5 min. of making a seal, with access resistances between 10 to 20 M$\Omega$. The amplifier (Axopatch 2D, Axon Instruments) is then switched to current clamp mode and the neuron is stimulated by repeated pulses of depolarizing steps. When necessary, current was injected to keep the resting potential at approximately −65 mV. The potential is digitized, stored and analyzed using Superscope (GW Instruments) and an A/D board (GW Instruments).

Detecting Action Potentials in "Follower" Cells.

For this protocol, use is made of the fact that action potentials produce stereotyped calcium influxes in the somata of neocortical neurons (Helmchen et al., 1996; Smetters et al., 1999) to detect which neuron in the imaged field is spiking after the stimulation of the "trigger" cell. Although the patched cell is originally loaded with fura-2 AM, the establishment of a whole cell recording dilutes the indicator. Because of this, fura-2 is routinely included in the pipette in order to also image the calcium transients of the patched cell. To enable the comparison of the calcium signals between the patched and the other cells, a concentration of fura-2 (50 $\mu$M, unless otherwise specified) similar to the concentration of fura-2 estimated for the AM loaded cells is used.

Figure 2A:
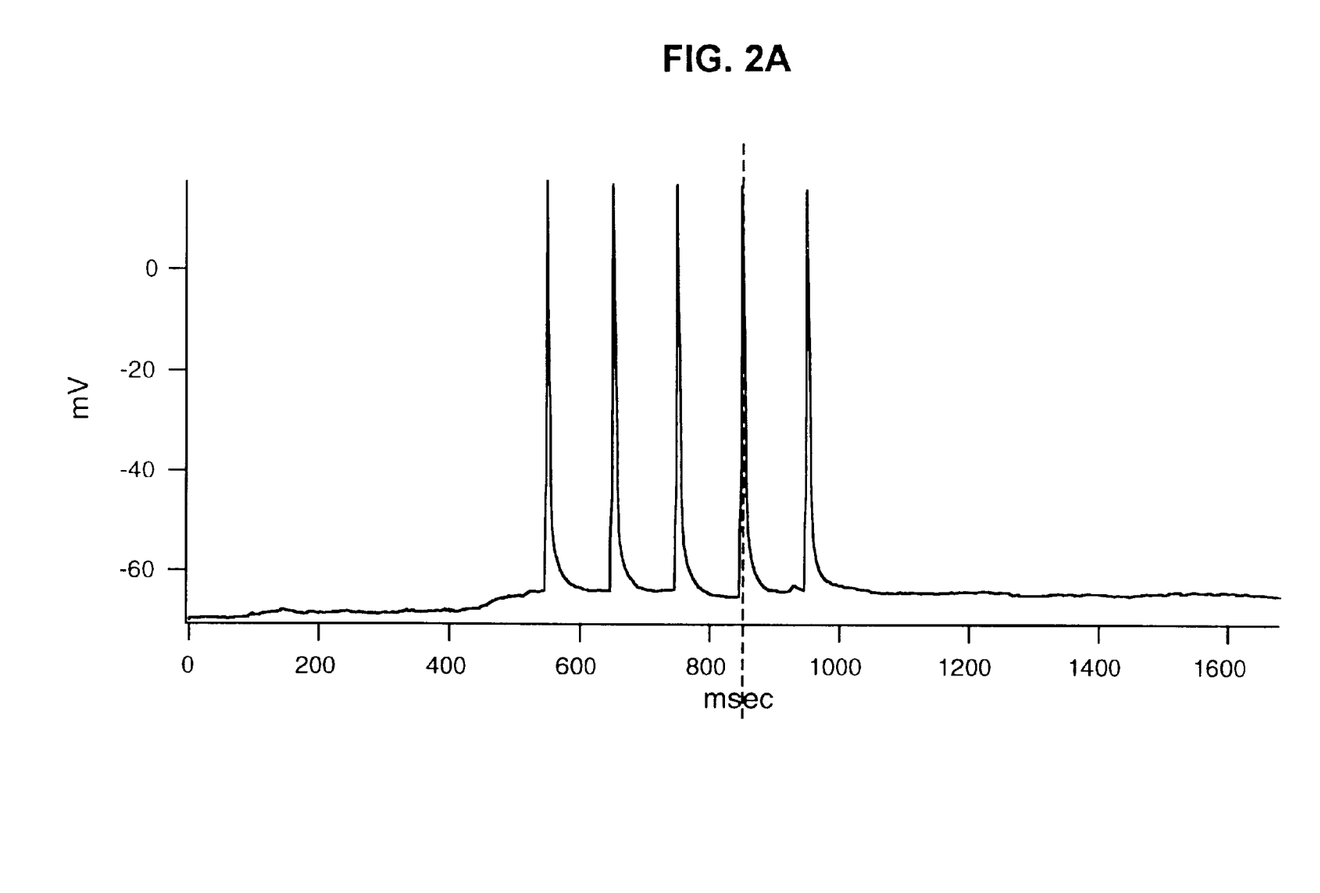
FIG. 2A: Whole cell recording of the voltage of neuron 1 ("trigger"). In response to five depolarizing current pulses (3 nA, 5 msec) the neuron fires five action potentials. Resting potential was −70 mV.
Figure 2B:
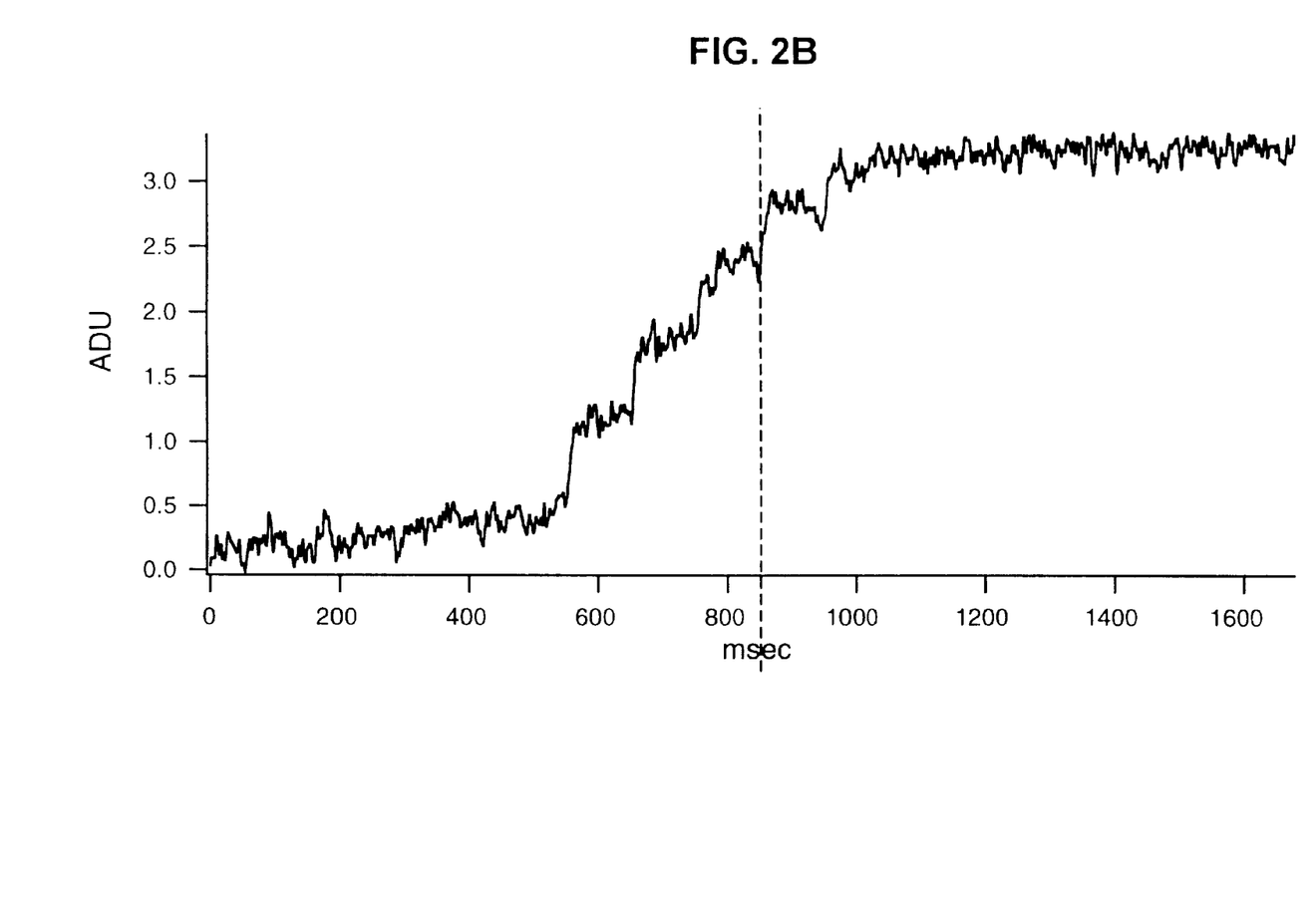
FIG. 2B: Simultaneous fluorescence measurements of the somatic region of neuron 1 shows discrete decrements in fluorescence which correspond to the five action potentials. Neuron 1 was filled with 100 $\mu$M fura-2. At 380 nm excitation decreases in fluorescence correspond to increases in $[Ca^{2+}]_i$.

The patched neuron is stimulated to fire a train of action potentials by injecting pulses of depolarizing current (FIG. 2A). Each action potential produces a stereotyped calcium transient in the soma of the patched neuron, with peak amplitudes of 1–5% $\Delta F/F$, time to peaks of approximately 10 msec and long decays, which can last for several seconds (FIG. 2B). Depolarizing pulses which do not reach threshold do not result in any calcium accumulations. Because the onset of the calcium transient occurs within less than 1 msec from the peak of the action potential, using high temporal resolution imaging (0.6 msec per data point) of the calcium transient the occurrence of each action potential in the patched cell can therefore be accurately followed, as well as in all other imaged cells in the slice.

Figure 2C:
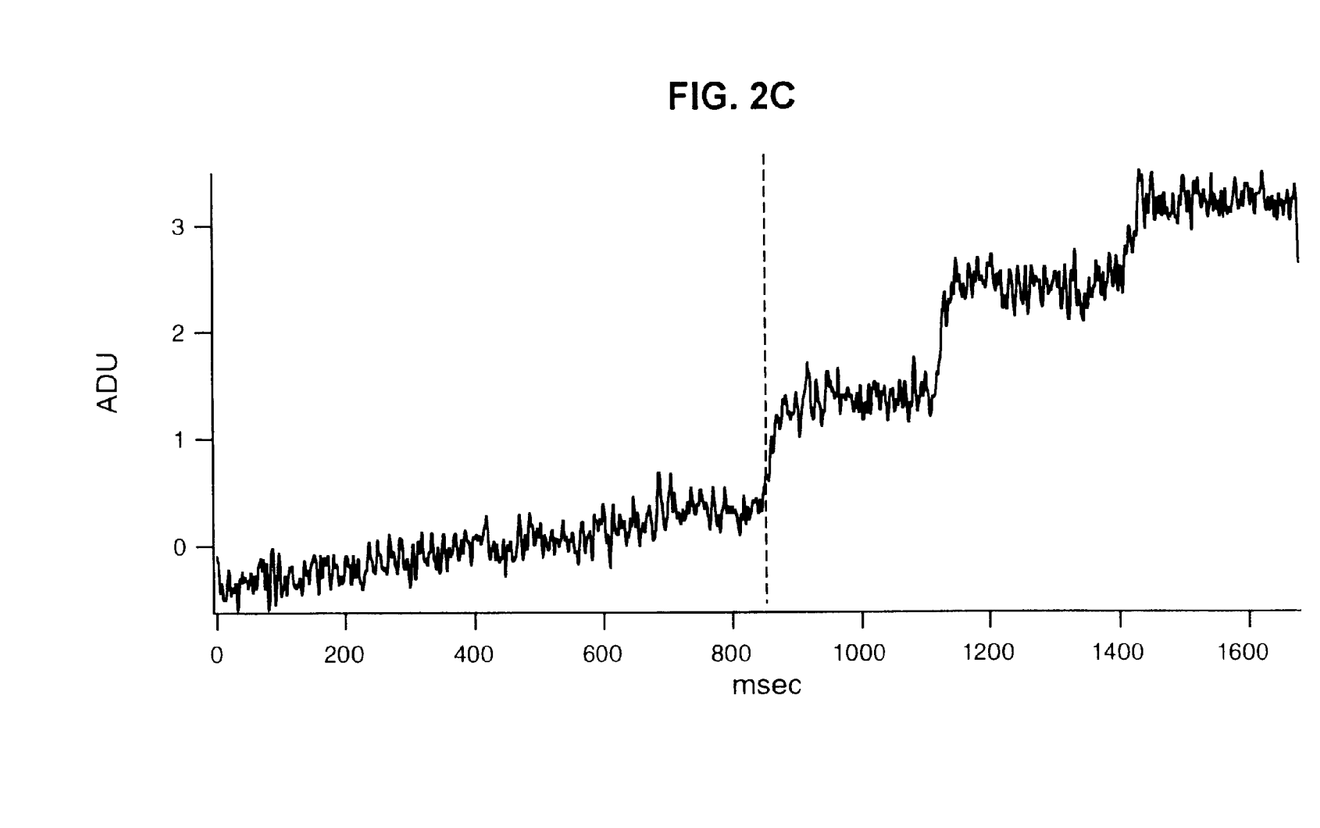
FIG. 2C: Simultaneous fluorescence measurements of neuron 2 ("follower") showing a calcium increase (fluorescence decrease) phase-locked with the 4th action potential of neuron 1. The onset of the calcium signal in neuron 2 occurs coincident with the peak of the action potential in neurons 1.
Figure 2D:
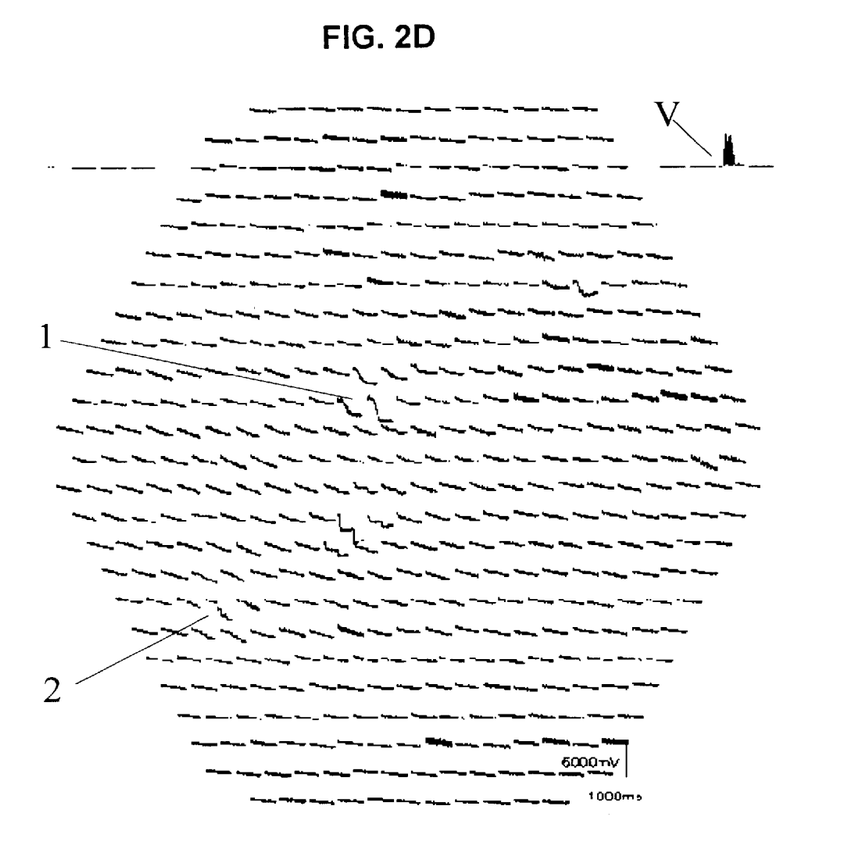

In many experiments, stimulation of the "trigger" cell with a train of action potentials produces secondary calcium increases in other neurons (FIGS. 2C and 2D) Due to the similarity in amplitude and kinetics of the responses in the "follower" cells to those elicited by a single action potential in the "trigger" cell, it is reasoned that the responses are produced by single action potentials and conclude that the secondary neurons have been brought to action potential threshold by the stimulation of the "trigger" cell. The delay between the action potential peak of the "trigger" cell and the onset of calcium accumulation of the "follower" cells is in most instances less than 5 msec. Taking into account delays in axonal propagation, synaptic transmission and voltage accumulation of EPSPs to reach threshold, this suggests that the "follower" cell is monosynaptically connected to the "trigger" cell. Nevertheless, in other cases longer delays (up to 100 msec) have also been noticed between the action potential in the trigger cell and the onset of a calcium response in the follower cell.

Since, under standard recording conditions, the spontaneous activation of an imaged neuron is rarely detected, these longer delays are interpreted as an indication of the activation of a polysynaptic chain of neurons, triggered by the activation of a "trigger" cell.

Optimization of the Experimental Procedure

Figure 3A:
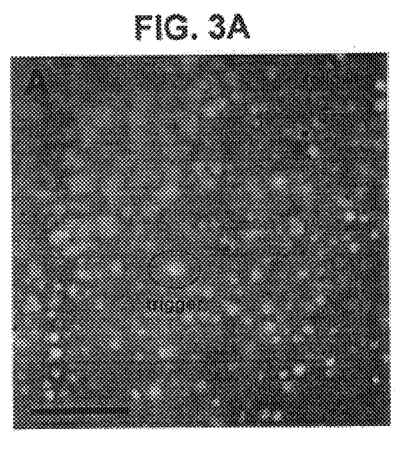
FIG. 3A: Fluorescence image of a coronal slice from P12 mouse visual cortex showing the relative location of the trigger and follower cells. The area imaged was a region of layer 5 approximately 375×375 $\mu$m with the pial surface to the upper left. The follower cell is boxed to the upper right. The slice was stained with fura-2-AM as described above.
Figure 3B:
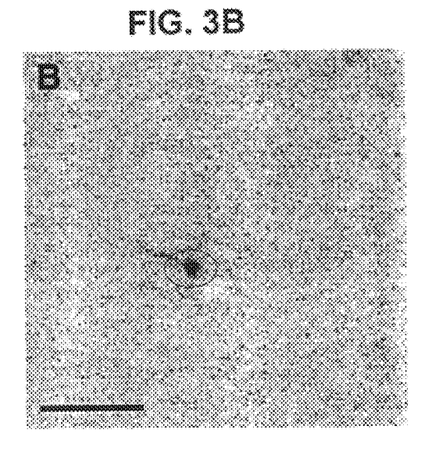
Figure 3C:
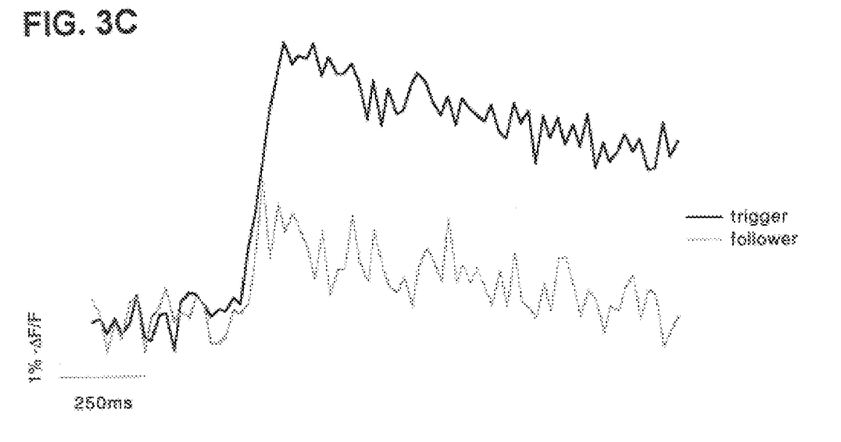
FIG. 3C: Image of the fluorescence measurements at the soma of the trigger and follower cells. At 380 nm excitation, decreases in fluorescence correspond to increases in $[Ca^{2+}]i$. The onset of the calcium signal in the follower cell occurs within 25 ms of the onset in the trigger cell, the limit of resolution for this movie (exposure time=25 ms/frame).

To maximize the number of followers the detection of the signals has been optimized and different stimulation paradigms and different conditions that would change the excitability of the brain slice have been experimented with. To optimize the detection of action potentials in the imaged neurons the imaging and analysis protocols have been tailored to the average kinetics of the action-potential signals. Thus, with the cooled charge couple device (cCCD) camera relatively slow acquisition rates (~25 msec/frame) are used to image the falling phase of the calcium transient. Those movies are analyzed by making a processed $\Delta F/F$ movie and adjusting the LUT so that the pixels where calcium increases appear in white over a black background. This enables the on-line (<3 minute) detection of any imaged neuron that produces a calcium transient larger than 0.5% $\Delta F/F$ (FIG. 3). Finally, since the follower neurons may not necessarily be in the same focal plane as the trigger cell, neurons are routinely screened at different focal planes from the stimulated one.

Different stimulation protocols have been experimented with. In agreement with the small size of single-axon cortical EPSPs (Mason and Larkman, 1990; Deuchards et al., 1994; Markram and Tsodyks, 1996), responses in secondary neurons after a single action potential stimulation of the patched neuron have never been detected. Nevertheless, with trains of action potentials, activation of follower neurons happens readily. Currently used are stimulation protocols of 10 spikes at 40 Hz, to take advantage of paired-pulse facilitation. Longer trains or higher frequencies have not successfully increased the yield of the experiment.

To maximize the effect of the stimulation of the trigger cell, different methods of enhancing synaptic release and also of making postsynaptic cells more excitable have been experimented with. Currently used is 3 mM $[Ca^{2+}]_e$ in our ACSF (artificial cerebrospinal fluid) because high $[Ca^{2+}]_e$ decreases synaptic failures and, by increasing the $[Ca^{2+}]$ gradient between the inside and outside of the cell, it also produces bigger action-potential induced calcium signals. We also routinely use nominally 0 mM $[Mg^{2+}]_e$ ACSF, in order to unblock NMDA (N-methyl-D-aspartate) receptors and increase the effect of EPSP's (excitatory postsynaptic potentials). Making the slice more excitable by use of blockers of GABA-A receptors (Bicuculine) or potassium channel blockers (TEA or 4-AP), in these experiments, increases the number of possible postsynaptic targets. Unfortunately, it also produces spontaneous or evoked epileptiform events where most or all of the imaged neurons show action-potential induced increases in $[Ca^{2+}]_i$.

Confirmation of Synaptic Contact

It has been noticed that follower cells can be time-locked to the trigger cell in more than one trial, indicating that they are indeed connected. Interestingly, they do not follow the trigger cell in all trials. This lack of reliable excitation between different trials could be due to the stochastic nature of synaptic transmission or to synaptic fatigue or depression after repeated stimulation trains.

Figure 4A:
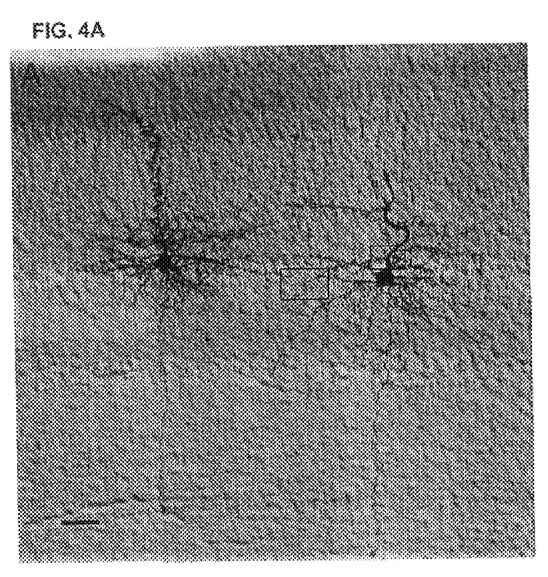
FIG. 4A. DIC photomicrograph of the two patched cells from FIG. 3, after biocytin processings. Axonal and dendritic arbors from each cell are easily distinguished. The cell on the right is the "trigger" cell and the cell on the left is the "follower" cell. Scale bar=50 $\mu$m.
Figure 4B:
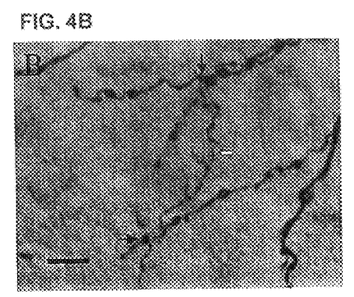
Figure 4C:
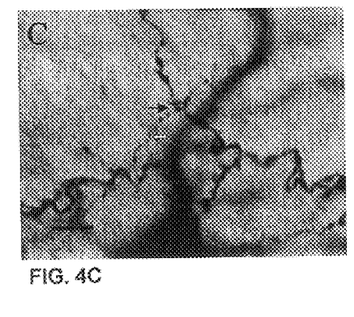

To confirm the synaptic contact between the trigger and follower cells anatomical reconstruction of the neuron was used. Biocytin (0.5–1%) is routinely included in the trigger cell to enable the reconstruction of its axonal arbor using the standard ABC method (Vector). Because the detection of the follower cell can be done on-line, it is possible to patch it (FIG. 3) and also fill it with biocytin. In several instances it has been possible to trace the axon of the trigger cell to one of the dendrites of the follower cells (FIG. 4). With the resolution of the light microscope the axon appears to physically contact the dendrite in at least one position.

Therefore, three different lines of evidence are presented here that suggest that the trigger and follower cells are synaptically connected. First, the response of the follower cell is time-locked to an action potential of the trigger cell. Second, the follower cell can be activated by stimulation of the trigger cell in more than one trial. Third, the axon of the trigger cell can always be traced to the dendrites of the follower cell. Taken together, the present data strongly indicate that the trigger cell forms axon-dendritic synaptic contacts with the follower cell.

Discussion

Advantages of Optical Probing

The main advantage of this technique ("optical probing") is to quickly identify target cells of a given neuron. Thus, it can be used as an assay to visually select which neuron to patch in dual recording experiments, which have previously been done blindly. Since the patching of a trigger cell and the detection of a follower can be completed in less than ten minutes, this technique could be used in series to quickly identify polysynaptic circuits, or even reconstruct the entire circuit diagram within the same brain slice.

Another advantage is that stronger connections will be revealed at the expense of weaker, presumably less important, ones. Because this assay requires the suprathreshold depolarization of the postsynaptic neuron, connections made with multiple contacts, or with synapses of higher efficacy, would be the first ones to be detected. Connections with fewer or weaker terminals will produce subthreshold events that will not be detected unless the postsynaptic neurons are brought to near threshold using one of the above-mentioned strategies. This may be a major advantage in areas with abundant distributed weak connections, since it will allow the investigator to concentrate on the study of those connections likely to be more effective in driving the circuit.

Optical probing also serves as an assay of the function of a particular connection or a circuit. Thus the effect of neuromodulators or pharmacological agents can be quickly tested. Given the enormous diversity of effects of neuromodulators and drugs on neurons in the central nervous systems, where sometimes the same substance can have opposite effects on neighboring neurons in the same area (McCormick, 1992), the ability to quickly assay single identified connections, or a series of those forming a circuit, provides an application for optical probing.

A consequence of this is that the strength and reliability of individual synaptic connections can be tested in parallel. Thus, studies of plasticity of single connections can be done simultaneously in multiple postsynaptic neurons, after stimulating the presynaptic neuron with different patterns of activation that could induce potentiation or depression in different target cells. By monitoring their suprathreshold responses, the effect of different temporal patterns of presynaptic stimulation on synaptic transmission can be investigated simultaneously in many neurons.

Finally, a major advantage of this technique is that it does not require expensive equipment. Because of the relatively large amplitude of the optical signals (that can be several % in ΔF/F peak amplitude), these experiments have succeeded in detecting single action potentials in neuronal populations using SIT cameras (Hamamatsu and Dage), 8-bit digitization boards present in standard personal computers (Power Macintosh 7600 and 7500) and freeware analysis packages (NIH Image). The essential form of this experiment therefore can be carried out with easily accessible equipment present in most neurobiological research institutes.

A problem with this optical probing approach is the necessity for the trigger cell to be an excitatory neuron, so it only reveals excitatory connections. Two possible modifications of the technique will allow detection of inhibitory connections. One would be the imaging of the population under conditions of high background spontaneous activity, induced by any of the pharmacological manipulations described above. In this case, stimulation of an inhibitory "trigger" cell should produced a time-locked inhibition of the action potentials of the "follower" cells.

An alternative strategy to image inhibitory connections is to use $Cl^-$ indicators, since the action of the major inhibitory neurotransmitter in the central nervous system, GABA, occurs with the gating of a $Cl^-$ channel, the GABAA receptor. Therefore $Cl^-$ flux in postsynaptic neurons signals the activation of inhibitory connections. The optimal $Cl^-$ sensitive dyes would need to be sensitive to submillimolar changes in the range of 10 mM intracellular $Cl^-$. The indicator MEQ (Molecular Probes) shows the greatest changes in fluorescence with small changes in Cl⁻ between 0 and 10 mM. MEQ can be converted to a lipophylic Cl⁻ insensitive compound for loading into cells by using the reducing agent sodium borohydride. This enables MEQ to cross cell membranes and get into the cytosol, where it is reoxidized to the Cl⁻ sensitive form of MEQ, thus making it ideal for loading multiple cells in slice. Because many inhibitory contacts target somatic regions, the imaging of somata could enable the optical detection of IPSPs (inhibitory postsynaptic potentials).

A second problem with this approach is that this optical probing can only reveal suprathreshold connections. The experiments have never detected somatic calcium accumulations in response to subthreshold EPSPs. This agrees with the data herein using two-photon excitation showing that subthreshold EPSPs produce calcium accumulations localized to individual dendritic spines (Yuste and Denk, 1995). As explained, it is thought that this insensitivity to subthreshold connections should be an advantage when analyzing circuits with distributed connectivity. Nevertheless, for cases where it becomes necessary to reveal as many subthreshold connections as possible, manipulations of the excitability of the slice, like those outlined above, can easily be combined with this technique to turn initially subthreshold events into suprathreshold ones and thus reveal a larger selection of postsynaptic targets.

A final disadvantage of this technique is that it can only be applied in regions where brain slices can be made and at ages where bulk-loading of calcium indicators is robust. So far, the experiments have not been successful in loading rodent cortical slices older than P25. While novel techniques could solve this problem (see below), it is thought that, in the case of the rodent cortex, the optical probing method described herein already opens experimental access to circuits at mature postnatal ages past the critical period of development.

One of the most exciting prospects of this technique is its combination with genetically-encodable activity-sensitive indicators, like green fluorescent protein (GPF)-based indicators, e.g. calmodulin-GFP indicators (Miyawaki et al., 1997; Garamszegi et al., 1997) or potassium-channel GFP constructs (Siegel and Isacoff, 1997). Besides possible improvements in signal to noise and direct measurements of voltage transients, these or other similar indicators could be expressed in particular sets of neurons, thus enabling the piecemeal analysis of the circuits. Also, transgenic animals expressing these indicators in cortical neurons will enable in vivo experiments, using the depth penetration of two-photon excitation microscopy (Denk et al., 1994).

Finally, another exciting avenue for future improvements is to combine this technique with cross-correlations analysis of the spontaneous or evoked activity of groups of neurons (Schwartz et al., 1998). The development of fast algorithms to detect multineuronal correlations that can be used on-line during an experiment (Kumar and Yuste, in prep.) should permit the detection of particularly interesting neurons in a circuit, which could then be patched in order to reconstruct its target identified with this optical probing. As an ideal version of this experiment, the use of dual-caged glutamate (Pettit et al., 1997) under computer-control laser uncaging (Katz and Dalva, 1994) could enable an all-optical stimulation and detection of circuit connectivity.

References

Buhl E. H., Halasy K., Somogyi P. (1994). Diverse sources of hippocampal unitary inhibitory postsynaptic potentials and the number of synaptic release sites. Nature 368, 823–828.

Czeiger D., White E. L. (1993). Synapses of extrinsic and intrinsic origin made by callosal projection neurons in mouse visual cortex. J. Comp. Neurol. 330, 502–13.

Denk W., Delaney K. R., Gelperin A., Kleinfeld D., Strowbridge B. W., Tank D. W., Yuste R. (1994). Anatomical and functional imaging of neurons using 2-photon laser scanning microscopy. J. Neurosci. Meth. 54, 151–162.

Deuchards J., West D. C., Thomson A. (1994). Relationships between morphology and physiology of pyramid—pyramid single axon connections in rat neocortex in vitro. J. Neurophysiol. 478, 423–435.

Garamszegi N., Garamszegi Z. P., Rogers M. S., DeMarco S. J., Strehler E. E. (1997). Application of a chimeric green fluorescent protein to study protein—protein interactions. Biotechniques 23, 846–6.

Gulyas A. I., Miles R., Sik A., Toth K., Tamamaki N., Freund T. F. (1993). Hippocampal pyramidal cells excite inhibitory neurons through a single release site. Nature 366, 683–687.

Heiligenberg W. (1991). Neural Nets in Electric Fish. Computational Neuroscience Series. Cambridge, Mass.: MIT Press.

Helmchen F., Imoto K., Sakmann B. (1996). Ca2+ buffering and action potential-evoked Ca2+ signalling in dendrites of pyramidal neurons. Biophys. J. 70, 1069–1081.

Katz L. C., Dalva M. (1994). Scanning laser photostimulation: a new approach for analyzing brain circuits. J. Neurosci. Meth. 54, 205–18.

Macagno E. R., Levinthal C., Soberl I. (1979). Three-dimensional computer reconstruction of neurons and neuronal assemblies. Annu. Rev. Biophys. Bioeng. 8, 323–351.

Markram H., Tsodyks M. (1996). Redistribution of synaptic efficacy between neocortical pyramidal neurons. Nature 382, 807–810.

Mason A., Larkman A. (1990). Correlations Between Morphology and Electrophysiology of Pyramidal Neurons in Slices of Rat Visual Cortex. II. Electrophysiology. J. Neurosci. 10, 1415–1428.

McCormick D. A. (1992). Neurotransmitter actions in the thalamus and cerebral cortex and their role in neuromodulation of thalamocortical activity. Prog. Neurobiol. 39, 331–388.

McGuire B. A., Gilbert C. D., Rivlin P. K., Wiesel T. N. (1991). Targets of horizontal connections in macaque primary visual cortex. J. Comp. Neurol. 305, 370–92.

Meister M., Pine J., Baylor D. A. (1994). Multi-neuronal signals from the retina: acquisition and analysis. J. Neurosci. Meth. 51, 95–106.

Meister M., Wong R. O. L., Baylor D. A., Shatz C. J. (1991). Synchronous bursts of action potentials in ganglion cells of the developing mammalian retina. Science 252, 939–943.

Miyawaki A., Llopis J., Heim R., McCaffery J. M., Adams J. A., Ikura M., Tsien R. Y. (1997). Fluorescent indicators for Ca2+ based on green fluorescent proteins and calmodulin. Nature 388, 882–7.

O'Donovan M. J., Ho S., Sholomenko G., Yee W. (1993). Real-time imaging of neurons retrogradely and anterogradely labelled with calcium-sensitive dyes. J. Neurosci. Meth. 46, 91–106.

Pettit D. L., Wang S. S., Gee K. R., Augustine G. J. (1997). Chemical two-photon uncaging: a novel approach to mapping glutamate receptors. Neuron 19, 465–71.

Schwartz T., Rabinowitz D., Unni V. K., Kumar V. S., Smetters D. K., Tsiola A., Yuste R. (1998). Networks of coactive neurons in developing layer 1. Neuron 20, 1271–1283.

Siegel M. S., Isacoff E. Y. (1997). A genetically encoded optical probe of membrane voltage. Neuron 19, 735–41.

Smetters D. K., Majewska A., Yuste R. (1999). Detecting action potentials in neuronal populations with calcium imaging. Methods 18, (in press).

Tsien R. Y. (1981). A non-disruptive technique for loading calcium buffers and indicators into cells. Nature 290, 527–528.

White E. L., Amitai Y., Gutnick M. J. (1993). A novel approach to correlative studies of neuronal structure and function. Isr. J. Med. Sci. 29, 549–55.

White J. G., Southgate E., Thomson J. N., Brenner S. (1986). The structure of the nervous system of the nematode caenorhabditis elegnas. Philos. Trans. R. Soc. Lond. (Biol). 314, 1–340.

Yuste R. (1999) Loading populations neurons in slices with AM calcium indicators. In: Imaging: a laboratory manual, R. Yuste, F. Lanni and A. Konnerth, ed. (Cold Spring Harbor: Cold Spring Harbor Press) (in press)

Yuste R., Denk W. (1995). Dendritic spines as basic units of synaptic integration. Nature 375, 682–684.

Yuste R., Katz L. C. (1991). Control of postsynaptic Ca2+ influx in developing neocortex by excitatory and inhibitory neurotransmitters. Neuron 6, 333–344.

What is claimed is:

1. A method of identifying if a connection exists between a first neuron and a second neuron in a neural tissue slice comprising:
   a) loading the neural tissue slice containing the first neuron and the second neuron with a fluorescent indicator which fluoresces in response to neuronal calcium influx;
   b) measuring the fluorescence of the second neuron after the neural tissue slice is loaded with the fluorescent indicator in step (a);
   c) stimulating the first neuron in the neural tissue slice so as to elicit an action potential from the first neuron; and
   d) measuring the fluorescence of the second neuron in response to the action potential elicited from the first neuron in step (c),
wherein measurement of a transient change in the fluorescence of the second neuron in step (d) as compared to the measurement of the fluorescence of the second neuron in step (b) identifies that a connection exists between the first neuron and the second neuron in the neural tissue slice.

2. The method of claim 1 wherein the fluorescent indicator is a fluorescent dye.

3. The method of claim 2, wherein the fluorescent indicator is fura-2 AM, calcium green AM, Oregon BAPTA Green AM or indo-2 AM.

4. The method of claim 1, wherein the first neuron is stimulated in step (c) with repeated pulses of depolarizing current at 10–100 Hz.

5. The method of claim 1, wherein the neural tissue is mammalian central nervous system or peripheral neurons.

6. The method of claim 1, wherein the fluorescence in steps (b) and (d) is measured with a camera.

7. The method of claim 1, wherein measuring the fluorescence in step (d) comprises measuring a percent change of fluorescence over time, said percent change calculated as $\Delta F/F = ((F_0 - B_0) - (F_1 - B_1))/F_0 - B_0)$, wherein $F_0$ is the fluorescence of the second neuron after loading and $B_0$ is the background fluorescence after loading, $F_1$ is the fluorescence of the second neuron at one time point after stimulation in step (c), and $B_1$ is the background fluorescence at said time point after stimulation in step (c).

8. A method of determining the effect of a neuromodulator on a connection between a first neuron and a second neuron in a neural tissue slice which comprises:
   a) loading the neural tissue slice containing the first neuron and the second neuron with a fluorescent indicator which fluoresces in response to neuronal calcium influx;
   b) measuring the fluorescence of the second neuron after the neural tissue slice is loaded with the fluorescent indicator in step (a);
   c) administering a neuromodulator to the neural tissue slice and eliciting an action potential from the first neuron; and
   d) measuring the fluorescence of the second neuron in response to the action potential elicited from the first neuron in step (c),
wherein measurement of a transient decrease or increase in the fluorescence of the second neuron indicates, respectively, an increase or decrease in the activation of the second neuron, thereby determining the effect of the neuromodulator on the connection between the first neuron and the second neuron in the neural tissue slice.

9. The method of claim 8 wherein the neuromodulator is a neurochemical agent.

10. A method of identifying if an inhibitory connection exists between an inhibitory neuron and a second neuron of high spontaneous activity in a neural tissue slice comprising:
   a) loading the neural tissue slice containing the inhibitory neuron and the second neuron with a fluorescent indicator which fluoresces in response to neuronal calcium influx;
   b) measuring the fluorescence of the second neuron after the neural tissue slice is loaded with the fluorescent indicator in step (a);
   c) stimulating the inhibitory neuron in the neural tissue slice so as to elicit an action potential from the inhibitory neuron; and
   d) measuring the fluorescence of the second neuron in response to the action potential elicited from the inhibitory neuron in step (c),
wherein measurement of a decrease in the fluorescence of the second neuron in step (d) as compared to the measurement of the fluorescence of the second neuron in step (b) identifies that an inhibitory connection exists between the inhibitory neuron and the second neuron in the neural tissue slice.

11. A method of identifying if an inhibitory connection exists between an inhibitory neuron and a second neuron in a neural tissue slice comprising:
   a) loading the neural tissue slice containing the inhibitory neuron and the second neuron with a fluorescent chloride indicator;
   b) measuring the fluorescence of the second neuron after the neural tissue slice is loaded with the fluorescent indicator in step (a);
   c) stimulating the inhibitory neuron in the neural tissue slice so as to elicit an action potential from the inhibitory neuron; and
   d) measuring the fluorescence of the second neuron in response to the action potential elicited from the inhibitory neuron after stimulating in step (c),
wherein measurement of a transient change in the fluorescence of the second neuron identifies that an inhibitory connection exists between the inhibitory neuron and the second neuron in the neural tissue slice.

12. The method of claim 11, wherein the chloride indicator is 6-methoxy-N-ethylquinolinium iodide.

13. A method of identifying a connection between a first neuron and a second neuron or plurality of neurons in vivo comprising of:
   a) genetically encoding a transgenic animal to express green fluorescent protein (GFP)-based indicators in a neural tissue;
   b) optically detecting an image of the GFP-based indicator in neurons of the neural tissue in the transgenic animal using a microscope or a two-photon microscope;

c) stimulating a first neuron in the neural tissue to elicit one action potential or multiple action potentials from said neuron or said neural circuit; and d) optically detecting a change in intensity of the GFP-based indicator in the image at a second neuron or plurality of neurons of the neural tissue in response to the action potential(s) elicited from the first neuron in step (c), wherein detection of a transient change in the intensity of the GFP-based indicator in the image at the second neuron or plurality of neurons indicates activation or inactivation of the second neuron or plurality of neurons, thereby identifying the connection between the second neuron or plurality of neurons and the first neuron.

14. The method of claim 13 wherein the transgenic animal is a mouse.

15. The method of claim 13 wherein the GFP-based indicator is selected from a cameleon or FLASH.

16. A method of identifying a connection between a first neuron and a second neuron or plurality of neurons in vitro comprising of:

a) optically detecting an image of a GFP-based indicator in neurons of a neural tissue slice from a transgenic animal whose neural tissue expresses the GFP-based indicator using a microscope or a two-photon microscope;

b) stimulating a first neuron in the neural tissue slice to elicit one action potential or multiple action potentials from said neuron; and c) optically detecting a change in intensity of the GFP-based indicator in the image at a second neuron or plurality of neurons of the neural tissue in response to the action potential(s) elicited from the first neuron in step (b), wherein detection of a transient change in the intensity of the GFP-based indicator in the image at the second neuron or plurality of neurons indicates activation or inactivation of the second neuron or plurality of neurons, thereby identifying the connection between the second neuron or plurality of neurons and the first neuron.

17. The method of claim 16 wherein the transgenic animal is a mouse.

18. The method of claim 16 wherein the GFP-based indicator is selected from a cameleon or FLASH.

19. A method of identifying if a connection exists between a first neuron and a plurality of neurons in a neural tissue slice comprising:

a) loading the neural tissue slice containing the first neuron and the plurality of neurons with a fluorescent indicator which fluoresces in response to neuronal calcium influx;

b) measuring the fluorescence of the plurality of neurons after the neural tissue slice is loaded with the fluorescent indicator in step (a);

c) stimulating the first neuron in the neural tissue slice so as to elicit an action potential from the first neuron; and d) measuring the fluorescence of the plurality of neurons in response to the action potential elicited from the first neuron after stimulating in step (c), wherein measurement of a transient change in the fluorescence of the plurality of neurons in step (d) as compared to the measurement of the fluorescence of the plurality of neurons in step (b) identifies that a connection exists between the first neuron and the plurality of neurons in the neural tissue slice.

20. A method of determining the effect of a neuromodulator on a connection between a first neuron and a plurality of neurons in a neural tissue slice which comprises:

a) loading the neural tissue slice containing the first neuron and the plurality of neurons with a fluorescent indicator which fluoresces in response to neuronal calcium influx;

b) measuring the fluorescence of the plurality of neurons after the neural tissue slice is loaded with the fluorescent indicator in step (a);

c) administering a neuromodulator to the neural tissue slice and eliciting an action potential from the first neuron; and d) measuring the fluorescence of the plurality of neurons in response to the action potential elicited from the first neuron in step (c), wherein measurement of a transient decrease or increase in the fluorescence of the plurality of neurons indicates, respectively, an increase or decrease in the activation of the plurality of neurons, thereby determining the effect of the neuromodulator on the connection between the first neuron and the plurality of neurons in the neural tissue slice.

21. A method of identifying if an inhibitory connection exists between an inhibitory neuron and a plurality of neurons of high spontaneous activity in a neural tissue slice comprising:

a) loading the neural tissue slice containing the inhibitory neuron and the plurality of neurons with a fluorescent indicator which fluoresces in response to neuronal calcium influx;

b) measuring the fluorescence of the plurality of neurons after the neural tissue slice is loaded with the fluorescent indicator in step (a);

c) stimulating the inhibitory neuron in the neural tissue slice so as to elicit an action potential from the inhibitory neuron; and d) measuring the fluorescence of the plurality of neurons in response to the action potential elicited from the inhibitory neuron in step (c), wherein measurement of a decrease in the fluorescence of the plurality of neurons in step (d) as compared to the measurement of the fluorescence of the plurality of neurons in step (b) identifies that an inhibitory connection exists between the inhibitory neuron and the plurality of neurons in the neural tissue slice.

22. A method of identifying if an inhibitory connection exists between a inhibitory neuron and a plurality of neurons in a neural tissue slice comprising:

a) loading the neural tissue slice containing the inhibitory neuron and the plurality of neurons with a fluorescent chloride indicator;

b) measuring the fluorescence of the plurality of neurons after the neural tissue slice is loaded with the fluorescent indicator in step (a);

c) stimulating the inhibitory neuron in the neural tissue slice so as to elicit an action potential from the inhibitory neuron; and d) measuring the fluorescence of the plurality of neurons in response to the action potential elicited from the inhibitory neuron after stimulating in step (c), wherein measurement of a transient change in the fluorescence of the plurality of neurons identifies that an inhibitory connection exists between the inhibitory neuron and the plurality of neurons in the neural tissue slice.

* * * * *